US011304621B2

(12) United States Patent
Merschon et al.

(10) Patent No.: US 11,304,621 B2
(45) Date of Patent: Apr. 19, 2022

(54) RADIATION-FREE POSITION CALIBRATION OF A FLUOROSCOPE

(71) Applicant: BIOSENSE WEBSTER (ISRAEL), LTD., Yokneam (IL)

(72) Inventors: Asaf Merschon, Karkur (IL); Eliahu Zino, Atlit (IL); Ofer Eliahu Klemm, Irvine, CA (US); Roy Urman, Karkur (IL); Ronen Krupnik, Karmiel (IL); Liron Shmuel Mizrahi, Kiryat Bialik (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 13/937,508

(22) Filed: Jul. 9, 2013

(65) Prior Publication Data
US 2015/0018668 A1 Jan. 15, 2015

(51) Int. Cl.
| A61B 90/00 | (2016.01) |
| A61B 34/00 | (2016.01) |
| A61B 5/06 | (2006.01) |
| A61B 6/00 | (2006.01) |
| A61B 5/00 | (2006.01) |
| A61B 34/20 | (2016.01) |

(52) U.S. Cl.
CPC ............ *A61B 5/061* (2013.01); *A61B 5/0071* (2013.01); *A61B 6/547* (2013.01); *A61B 2034/2051* (2016.02); *A61B 2090/364* (2016.02); *A61B 2090/376* (2016.02)

(58) Field of Classification Search
None
See application file for complete search history.

(56) References Cited

U.S. PATENT DOCUMENTS

| 5,255,680 | A | * | 10/1993 | Darrow et al. | 600/424 |
| 6,314,310 | B1 | * | 11/2001 | Ben-Haim et al. | 600/424 |
| 6,381,485 | B1 | | 4/2002 | Hunter et al. | |
| 8,057,394 | B2 | | 11/2011 | Dala-Krishna | |
| 2002/0193685 | A1 | * | 12/2002 | Mate | A61N 5/1049 600/424 |
| 2005/0228255 | A1 | * | 10/2005 | Saracen et al. | 600/407 |
| 2006/0009755 | A1 | | 1/2006 | Sra | |

(Continued)

FOREIGN PATENT DOCUMENTS

| CN | 2587369 A | 11/2003 |
| CN | 1469720 A | 1/2004 |

(Continued)

OTHER PUBLICATIONS

EP Search Report dated Nov. 21, 2014 for EP 14 17 6160.
(Continued)

*Primary Examiner* — Amelie R Davis
*Assistant Examiner* — Marjan Saboktakin
(74) *Attorney, Agent, or Firm* — Notaro, Michalos & Zaccaria P.C.

(57) ABSTRACT

A method includes registering a fluoroscopic imaging system and a position tracking system to a common frame of reference. A region of interest is marked in a patient body by the position tracking system. Using the common frame of reference, a field of view of the fluoroscopic imaging system is set such that the region of interest appears in the field of view.

14 Claims, 3 Drawing Sheets

(56) References Cited

U.S. PATENT DOCUMENTS

| | | |
|---|---|---|
| 2006/0116576 A1 | 6/2006 | McGee et al. |
| 2007/0055142 A1 | 3/2007 | Webler |
| 2007/0140427 A1 | 6/2007 | Jensen et al. |
| 2009/0171321 A1 | 7/2009 | Callaghan |
| 2011/0125150 A1* | 5/2011 | Deno ............ A61B 5/743 606/34 |
| 2012/0289821 A1 | 11/2012 | Graumann et al. |

FOREIGN PATENT DOCUMENTS

| | | | |
|---|---|---|---|
| CN | 1879574 A | | 12/2006 |
| JP | 08-196535 A | | 8/1996 |
| JP | H08196535 A | | 8/1996 |
| JP | 2000512189 A | | 9/2000 |
| JP | 2003-299642 A | | 10/2003 |
| JP | 2007526066 A | | 9/2007 |
| JP | 2009-502398 A | | 1/2009 |
| JP | 2012-170761 | * | 2/2011 |
| JP | 2012-000519 A | | 1/2012 |
| JP | 2012081167 A | | 4/2012 |
| JP | 2012170761 A | | 9/2012 |
| WO | WO 01/012057 A1 | | 2/2001 |
| WO | 2012090148 A1 | | 7/2012 |
| WO | WO 2012/090148 A1 | | 7/2012 |

OTHER PUBLICATIONS

Office Action and Search Report for corresponding Chinese application No. 201410325833.5, dated Sep. 30, 2017.

Japanese Office Action for corresponding Japan patent application No. 2014-140341, dated Jan. 23, 2018.

Translated Examiner's Decision of Refusal of corresponding Japanese patent application No. 2014-140341, dated Jun. 26, 2018.

Notification of Reasons for Refusal; Patent Application 2018-196516, dated Aug. 20, 2019.

Notification of Reasons for Refusal; Patent Application 2018-196516, dated Feb. 4, 2020.

* cited by examiner

RADIATION-FREE POSITION CALIBRATION OF A FLUOROSCOPE

FIELD OF THE INVENTION

The present invention relates generally to fluoroscopy, and particularly to methods for fluoroscope position calibration.

BACKGROUND OF THE INVENTION

Methods for locating the position of medical devices in the human body by magnetic and imaging procedures are known in the art. For example, U.S. Pat. No. 6,381,485, whose disclosure is incorporated herein by reference, describes a method for use during a procedure on a body. The method generates a display representing relative positions of two structures during the procedure. The method includes the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

U.S. Patent Application Publication 2007/0055142, whose disclosure is incorporated herein by reference, describes methods and apparatus for guiding the positioning of a device with a position tracking sensor and pre-recorded images. At least one embodiment uses pre-recorded time-dependent images (e.g., anatomical images or diagnostic images) to guide the positioning of a medical instrument (e.g., catheter tips) using real time position tracking during diagnostic and/or therapeutic operations with pre-recorded images. In one embodiment, predetermined spatial relations are used to determine the position of a tracked medical instrument relative to the pre-recorded images.

SUMMARY OF THE INVENTION

An embodiment of the present invention described herein provides a method including registering a fluoroscopic imaging system and a position tracking system to a common frame of reference. A region of interest is marked in a patient body by the position tracking system. Using the common frame of reference, a field of view of the fluoroscopic imaging system is set such that the region of interest appears in the field of view.

In some embodiments, registering the fluoroscopic imaging system and the position tracking system to the common frame of reference includes imaging using the fluoroscopic imaging system one or more objects having known coordinates in a first coordinate system of the position tracking system, and registering the first coordinate system of the position tracking system with a second coordinate system of the fluoroscopic imaging system using the imaged objects.

In other embodiments, setting the field of view includes positioning the fluoroscopic imaging system relative to the patient, without irradiating the patient with the fluoroscopic imaging system. In yet other embodiments, marking the region of interest includes measuring, using the position tracking system, respective positions of one or more sensors of the position tracking system that are positioned at known locations relative to the region of interest.

In some embodiments, measuring the positions includes locating one or more skin patch sensors of the position tracking system that are applied on a surface of the patient body. In other embodiments, measuring the positions includes locating one or more intra-body probes placed in the region of interest in the patient body. In yet other embodiments, the one or more probes include multiple probes, and marking the region of interest includes locating the region of interest based on multiple respective locations of the probes.

In some embodiments, marking the region of interest includes marking a fixed location in a three dimensional map of the region of interest produced by the position tracking system. In other embodiments, setting the field of view includes repositioning the patient body relative to the fluoroscopic imaging system so as to provide a largest overlap between the region of interest and the field of view.

In yet other embodiments, setting the field of view includes outputting instructions that direct an operator to reposition the field of view. In some embodiments, setting the field of view includes displaying an indication of the field of view, overlaid on a map of at least a part of the patient body produced by the position tracking system.

There is additionally provided herein, in accordance with an embodiment of the present invention, an apparatus including an interface and a processor. The interface is configured to communicate with a fluoroscopic imaging system and a position tracking system. The processor is configured to register the fluoroscopic imaging system and the position tracking system to a common frame of reference, to mark a region of interest in a patient body by the position tracking system, and, using the common frame of reference, to set a field of view of the fluoroscopic imaging system such that the region of interest appears in the field of view.

There is additionally provided herein a system, including a position tracking system, a fluoroscopic imaging system, and a fluoroscope position calibration system. The fluoroscope position calibration system is configured to register the fluoroscopic imaging system and the position tracking system to a common frame of reference, to mark a region of interest in a patient body by the position tracking system, and, using the common frame of reference, to set a field of view of the fluoroscopic imaging system such that the region of interest appears in the field of view.

The present invention will be more fully understood from the following detailed description of the embodiments thereof, taken together with the drawings in which:

DETAILED DESCRIPTION OF EMBODIMENTS

Overview

Embodiments of the present invention that are described herein provide improved methods and systems for calibrating the position of a fluoroscopic imaging system used for imaging an organ or cavity of a living body of a patient. The disclosed techniques set the fluoroscope position with minimal use of fluoroscopic radiation.

Position calibration of a fluoroscope typically involves repositioning the fluoroscope and/or the patient, so as to display the organ of interest at the center of the field of view of the fluoroscope system. Performing this process using the fluoroscopic imaging itself involves repeatedly repositioning the patient relative to the fluoroscope and acquiring a fluoroscopic image, until the organ of interest is centered within the field of view. In this iterative process, the patient is subjected to a high dosage of X-ray radiation.

In the embodiments described herein, the fluoroscopic imaging system operates in conjunction with a position tracking system that tracks a catheter inserted into the organ of interest (e.g., the patient heart). A calibration system is connected to the two systems and performs initial setting of the fluoroscopic system's field of view. The embodiments described herein refer mainly to magnetic-field-based position tracking systems, but the disclosed techniques can be used with various other types of position tracking systems, such as impedance-based systems.

Initially, the calibration system registers the fluoroscopic imaging system and the position tracking system to a common frame of reference. When using a magnetic position tracking system, for example, this registration may be performed by having the fluoroscopic system image the field generators of the magnetic position tracking system. The registration phase involves some fluoroscopic irradiation, but it is typically performed without the patient.

Then, the magnetic position tracking system marks the region of interest in the patient body, e.g., by measuring the position of the catheter or of skin patch sensors that are attached to the patient body in the vicinity of the region of interest. Using the common frame of reference, the calibration system repositions the field of view of the fluoroscopic imaging system such that that the region of interest appears in the field of view. This stage does not involve any fluoroscopic irradiation.

In some embodiments, the calibration system presents an operator with instructions or directions as to how to reposition the patient relative to the fluoroscope in order to bring the region of interest into the field of view. In other embodiments, the output of the calibration system can be used for automatic repositioning of the fluoroscope and/or the patient.

The methods and systems described herein enable quick and radiation-free initial positioning of the fluoroscopic imaging system relative to the patient.

System Description

Figure 1:
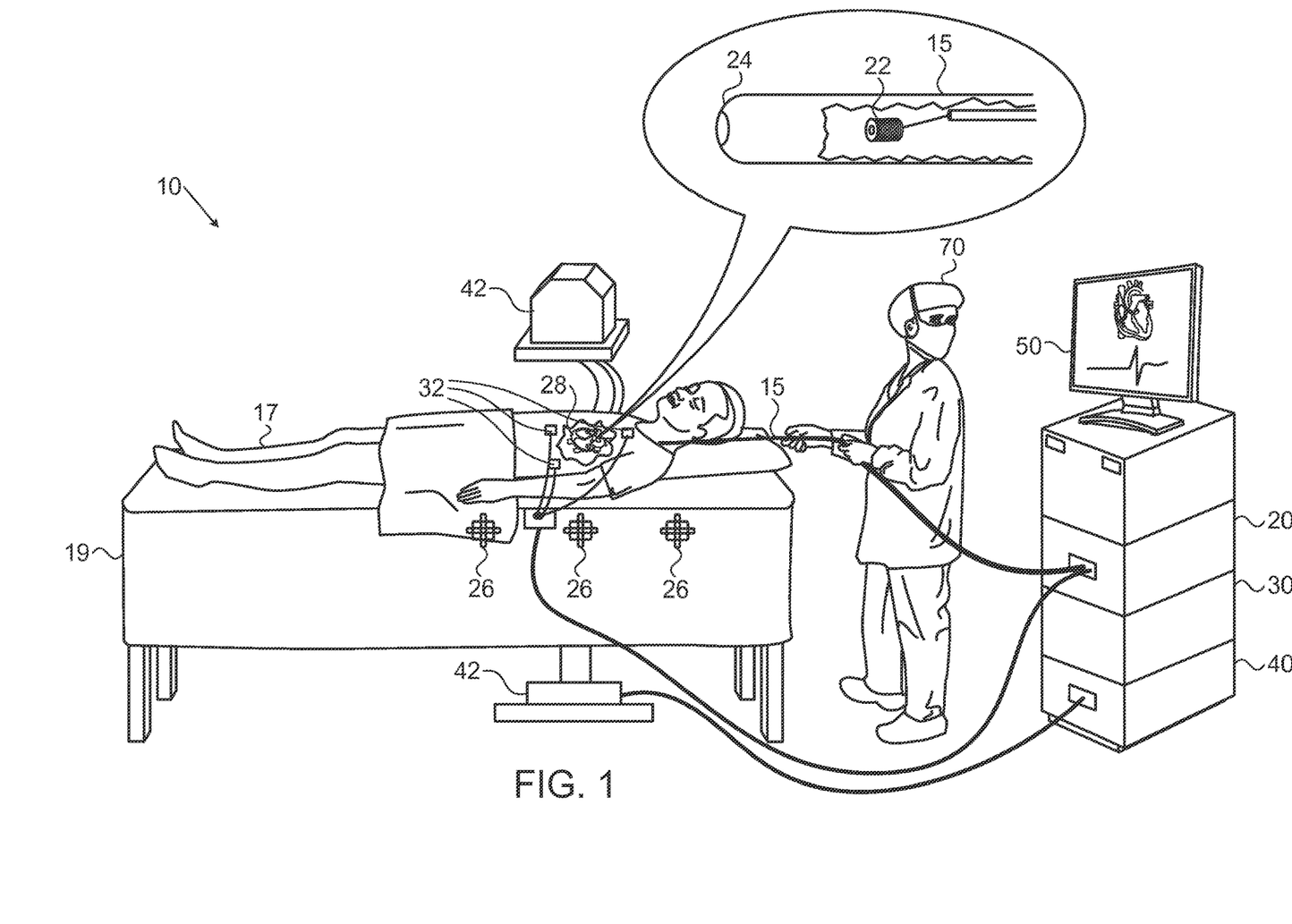
FIG. 1 is a schematic, pictorial illustration of an intra-body probe tracking system, in accordance with an embodiment of the present invention.

FIG. 1 is a schematic, pictorial illustration of an intra-body probe tracking system 10, in accordance with an embodiment of the present invention. An intra-body probe, such as a catheter 15, is connected to a magnetic tracking system (MTS) 20 and inserted percutaneously into a living body 17 of a patient laying on a gurney 19. Catheter 15 comprises a magnetic sensor coil 22 at a distal tip 24, which is navigated into an organ, such as a heart 28 of the patient. MTS 20 is also referred to herein as a magnetic position tracking system.

MTS 20 comprises one or more magnetic skin patch sensors 32 that are attached to a surface of patient body 17. One or more magnetic field generators 26 create a magnetic field through the body of the patient, which induces electrical signals in catheter magnetic sensor coil 22 and skin patch sensors 32. Field generators 26, which are also referred to herein as location pads or transmitter location pads, may be located under the patient. The induced electrical signals in catheter magnetic sensor coil 22 are used by MTS 20 to track and locate the position of sensor 22, and thus the catheter distal tip. The tracked position of the catheter distal tip is typically displayed to an operator 70 on an output display monitor 50.

Typically, skin patch sensors 32 also comprise similar coils as that of catheter magnetic sensor coil 22. The electrical signals induced in the coils of skin patch sensors 32 may also be used to locate the position of the skin patch sensors on the body. Examples of a magnetic tracking and three-dimensional (3D) mapping system 20 shown in FIG. 1, are the CARTO and CARTO3 systems (Biosense Webster, Diamond Bar, Calif.).

For many therapeutic and diagnostic medical procedures, such as cardiac ablation therapy, for example, MTS 20 is used in conjunction with imaging systems, such as a fluoroscope imaging system (FIS) 40. A fluoroscopic image of the heart, or any other suitable region of interest in the body, is acquired by a fluoroscopic detector 42 which is mounted above patient 17. The fluoroscopic image of the heart can be viewed on operator display 50 by operator 70 of the therapeutic procedure. Display 50 may comprise a separate display for FIS 40, or a common display for FIS 40 and MTS 20.

When the image on FIS 40 is registered to the same coordinate system (frame of reference) as MTS 20, the position of distal tip 24 of catheter 15 can be overlaid on the fluoroscopic image and viewed by operator 70 within the heart cavity of the patient as operator 70 moves the catheter during the procedure.

In some embodiments, a fluoroscope position calibration system 30 is used to position the image of heart 28 within a field of view of FIS 40 on display 50, as will be described below. The system configuration as shown in FIG. 1 is an exemplary configuration, which is shown purely for the sake of conceptual clarity. Any suitable configuration of system 10 may be used.

Figure 2:
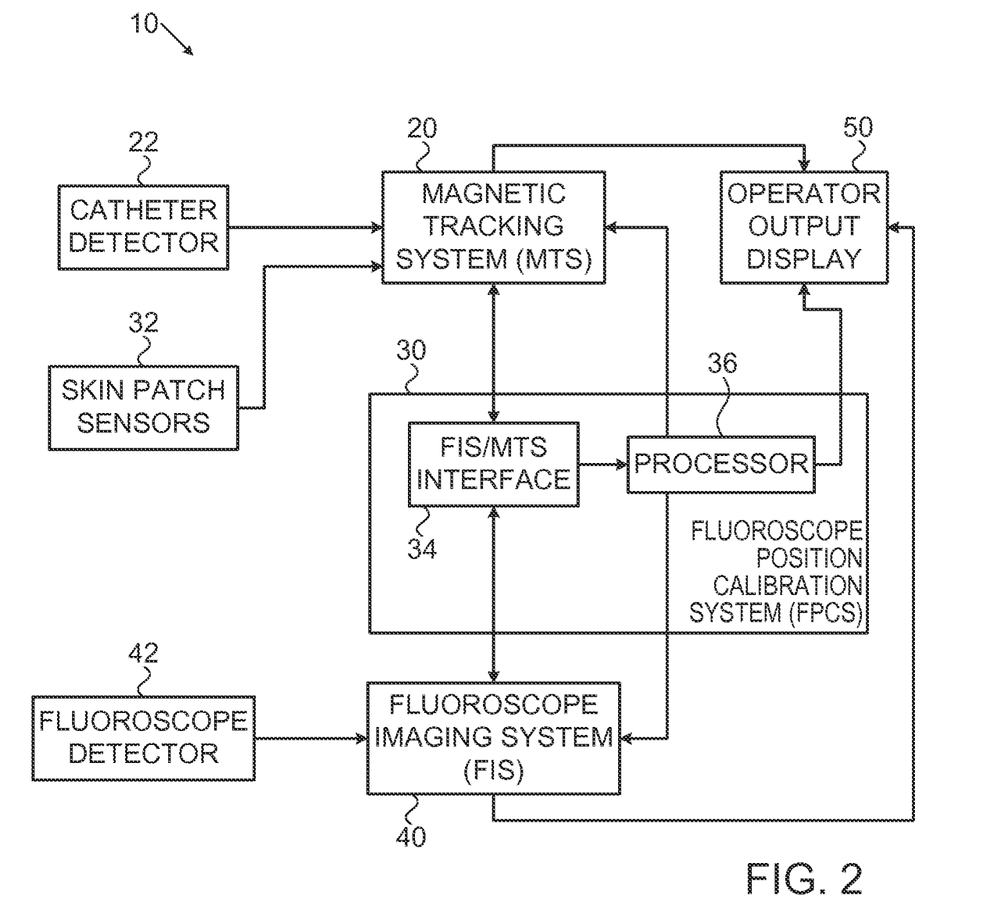
FIG. 2 is a block diagram that schematically illustrates an fluoroscopic position calibration system, in accordance with an embodiment of the present invention.

FIG. 2 is a block diagram that schematically illustrates fluoroscopic position calibration system (FPCS) 30, in accordance with an embodiment of the present invention. FPCS 30 in intra-body probe tracking system 10 comprises a FIS/MTS interface 34 for receiving data from MTS 20 and FIS 40, which is relayed to a processor 36 for processing. MTS 20 and FIS 40 send data respectively to operator output display 50. The input signals to MTS 20 as shown in FIG. 2 are from catheter detector 22 at the distal tip 24 of catheter 15 and skin patch sensors 32. Similarly, fluoroscopic detector 42 is the input to FIS 40. Processor 36 is configured to relay information as to the location of the skin patch sensors (e.g., the position of the heart) to both MTS 20 and FIS 40, and directly to operator output display 50.

The system configuration as shown in FIG. 2 is an exemplary configuration, which is purely for the sake of conceptual clarity. Alternatively, any other suitable system configuration can be used. For example, as noted above the disclosed techniques may be carried out using any other suitable type of position tracking system, not necessarily based on magnetic field measurements. Some elements of system 30 may be implemented in hardware, e.g., in one or more Application-Specific Integrated Circuits (ASICs) or Field-Programmable Gate Arrays (FPGAs). Additionally or alternatively, some elements of FPCS 30 can be implemented using software, or using a combination of hardware and software elements. In some embodiments, processor 36 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Synchronizing Tracking and Fluoroscope Reference Frames

Catheter tracking by MTS 20 is usually made with reference to an MTS frame of reference, or MTS coordinate system. The MTS frame of reference can also be referred to herein as a guidance frame of reference. MTS 20 registers the position of distal tip 24 of catheter 15 in the body of patient 17 using magnetic measurement data typically relative to the position of magnetic field generators 26 (location pads).

Fluoroscopic images of heart 28 in patient 17 are acquired, digitized, and registered by FIS 40 in a FIS frame of reference, or FIS coordinate system. Synchronizing the MTS and FIS coordinate systems to a common coordinate system, or common frame of reference, allows operator 70 to view and track the position of distal tip 24 of catheter 15 on the synchronized, digitized image of heart 28 on display 50 during the therapeutic procedure.

To synchronize the MTS and FIS coordinate systems, fluoroscopic images of known landmarks in system 10 are used. For example, the respective positions of one or more locations pads 26 (whose positions are known in the MTS coordinate system) are measured from fluoroscopic images acquired by FIS 40, and registered in the FIS coordinate system.

The FIS and MTS coordinate systems then are registered to a common frame of reference, or common coordinate system, using the position data of the location pads in the MTS and FIS coordinate systems. The synchronization of the MTS coordinate system with the FIS coordinate system and their respective registration to a common frame of reference are typically made before the patient is placed on gurney 19 as described above. Thus, this stage does not subject the patient to any radiation, and does not extend the length of the procedure.

Fluoroscope Position Calibration System (FPCS)

After synchronizing the MTS and FIS frames of reference, the patient is placed on the gurney, and operator 70 activates the fluoroscope. Typically, the operator then aligns fluoroscope detector 42 such that the region of interest, e.g., heart 28, appears in the center of the field of view of FIS 40 on display 50.

Embodiments of the present invention described herein avoid trial and error in attempting to center the region of interest into the field of view of the fluoroscope image display. The disclosed techniques perform this initial alignment without the need to apply additional radiation to the patient. This approach is in line with the "As Low As Reasonably Achievable" (ALARA) guidelines, which attempt to minimize patient irradiation.

In some embodiments, processor 36 of FPCS 30 finds the required repositioning of the patient relative to the FIS by (1) receiving from MTS 20 the coordinates of an object whose location relative to the region of interest is known, and (2) calculating the necessary repositioning using the coordinates of that object in the common frame of reference.

In various embodiments, processor 36 may use different objects for this purpose. In some embodiments, the objects comprise skin patch sensors 32 that are placed on the patient's skin at predefined known locations relative to the patient heart. As noted above, the skin patches are typically positioned around heart 28. Therefore, in some embodiments MTS 20 provides processor 36 with the measured coordinates of skin patches 32 (measured using magnetic position tracking). Using these coordinates, processor 36 is able to deduce the location of the region of interest (heart 28) in the common coordinate system, and thus calculate the required repositioning.

In other words, MTS 20 is activated so as to evaluate the position of skin patch sensors 32. Once the positions of sensors 32 are identified, the common frame of reference defined previously is then applied by fluoroscope position calibration system (FCPS) 30 to identify the position of the heart in the FIS frame of reference.

The identification of the location of the heart using skin sensors 32 and MTS 20 using the methods taught herein allow the operator to move the heart image into the field of view on display 50 without the use of any fluoroscope radiation during position calibration. The term position calibration, or radiation-free position calibration used herein refer to moving a region of interest of an organ in the body, (e.g., image of the heart) into a field of view of a fluoroscope imaging system. This process is typically performed before initiating the therapeutic procedure. However, fluoroscope 42 and/or patient 17 may be moved any time during the therapeutic procedure itself, after which position calibration is typically repeated. After position calibration, a fluoroscopic image of short duration is acquired for use in the normal therapeutic procedure in accordance with the ALARA guidelines.

In some embodiments, FPCS 30 is configured to alert operator 70 as to the direction in which to reposition patient 17 relative to fluoroscope detector 42. In other embodiments, FPCS 30 may instruct operator 70 as to the direction in which to move gurney 19 or fluoroscope detector 42 so as to bring the region of interest into the field of view on display 50. The instructions may be presented to the operator, for example, using textual or graphical indications on display 50.

Using the instructions provided by FPCS 30, the operator iteratively repositions the patient until the heart image appears in the field of view, quickly and without applying any fluoroscopic radiation to the patient. After fluoroscope detector 42 and/or gurney 19 are moved, if FPCS 30 validates that the region of interest is within the field of view on display 50, no further action is needed and the fluoroscope position calibration procedure is terminated.

In alternative embodiments, processor 36 may calculate the necessary repositioning of the FIS based on other suitable objects, whose location relative to the region of interest is known. In an example embodiment, one or more catheters fitted with position sensors (e.g., catheter 15 of FIG. 1) are inserted into the patient heart as part of the procedure. Since the catheter tips are known to be in the patient heart, the tip position (as measured by MTS 20) can be used as an indication of the location of the region of interest.

When multiple catheters are present in the heart, processor 36 may estimate the location of the region of interest based on the positions of the multiple catheters as reported by MTS 20. In example embodiments, processor 36 may calculate the median location of the catheters (intra-body probes) within the body of the patient, the location of a single catheter selected from among the catheters, e.g., the location of a catheter providing a specific function such as the mapping catheter in the CARTO3 system as referenced previously. As another example, the region of interest may be set to a fixed location in the 3D map of the heart (e.g., a map point, or anatomical landmark in the 3D map of the heart).

Further alternatively, processor 36 may define a sphere about the center of the region of interest. A predefined radius of the sphere can be either fixed or configurable by the operator. In other embodiments, the operator essentially centers the region of interest within a previously acquired two-dimensional image of the heart and then administers fluoroscopic radiation to validate the position of the region of interest.

In some embodiments, if the region of interest is larger than the field of view of FIS 40 on display 50, FPCS 30 may direct the operator how to reposition patient 17 on gurney 19, or fluoroscope detector 42, so as to achieve the best fit of the region of interest in the field of view of display 50. Stated differently, the best fit of the region of interest may be defined as where the largest portion of the region of interest overlaps the field of view on display 50.

Further alternatively, processor 36 may assess the required repositioning of the patient relative to the fluoroscope using any other suitable criterion and may generate any other suitable instructions for the operator. In yet another embodiment, the output of processor 36 may be used for automatically repositioning the patient and/or the fluoroscope with little or no operator involvement.

Processor 36 may use various kinds of Graphical User Interface (GUI) for indicating the alignment between MTS 20 and FIS 40 to operator 70. For example, processor 36 may overlay and display the 3D field-of-view of FIS 40 over the 3D map of the heart produced by MTS 20. The fluoroscope in FIS 40 typically has a 3D sector-shaped irradiation pattern (and field-of-view), e.g., pyramid-shaped or cone-shaped. In an embodiment, processor 36 displays this 3D sector-shaped irradiation pattern over the 3D EP map of the heart, which is produced by MTS 20. Both the FIS field-of-view and the EP map are displayed together, registered to the same coordinate system. This display provides the operator with an accurate and intuitive means for repositioning the patient or FIS in order to achieve best alignment.

The embodiment shown in FIGS. 1 and 2 shows a fluoroscopic position calibration system configured to use a magnetic catheter tracking system (such as the CARTO system previously cited) registered with a fluoroscopic imaging system to a common frame of reference. This exemplary embodiment is presented herein purely for conceptual clarity, and not by way of limitation of the embodiments of the present invention.

Alternatively, any other suitable type of position tracking system, such as electro-physiological (EP) catheter tracking systems or impedance-based Advanced Catheter Location (ACL), may be used so long as the coordinate system of the catheter tracking system can be registered with a fluoroscopic imaging system to a common frame of reference. Fluoroscope position calibration system 30 uses the common frame of reference to move the region of interest into the fluoroscopic system display as described in the embodiments herein.

Fluoroscope position calibration system 30 is also not limited to catheter position tracking systems, since millimeter-scale position accuracy is typically not required for the embodiments presented herein. For example, placing skin patch sensors 32, or any suitable electrophysiological (EP) sensors along any area on the patient's body, or within the patient's body can be used to define the region of interest using the location of the sensors. The region of interest is then registered in the common frame of reference with the fluoroscopic imaging system, and used by Fluoroscope position calibration system 30 to move the region of interest into the fluoroscopic display.

Figure 3:
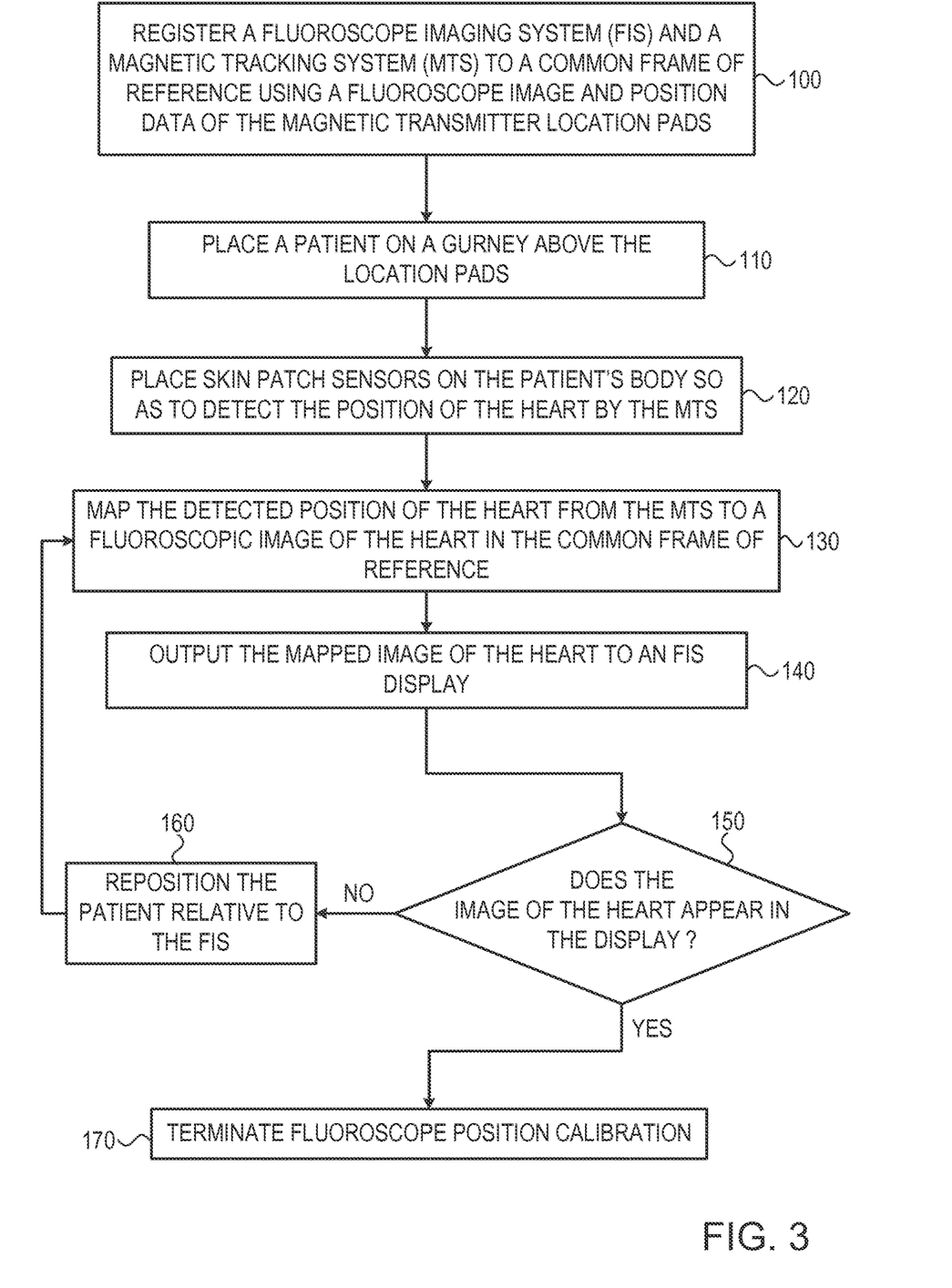
FIG. 3 is a flow chart that schematically illustrates a method for a radiation-free position calibration of a fluoroscope imaging system, in accordance with an embodiment of the present invention.

FIG. 3 is a flow chart that schematically illustrates a method for a radiation-free position calibration of fluoroscope imaging system 40, in accordance with an embodiment of the present invention. In a registering step 100, processor 36 registers fluoroscope imaging system (FIS) 40 and magnetic tracking system (MTS) 20 to a common frame of reference using a fluoroscope image and position data of magnetic location pads 26.

In a first placing step 110, patient 17 is placed on gurney 19 above location pads 26. In a second placing step 120, skin patch sensors 32 are placed on the patient's body so as to mark the position of heart 28 by MTS 20, which defines the region of interest for operator 70. In a mapping step 130, the detected position of the heart from MTS 20 is mapped to the fluoroscopic image of the heart in the common reference frame. In an outputting step 140, the mapped image of the heart is output to display 50.

In a decision step 150, processor 36 assesses if the region of interest appears centered in display 50, i.e., in the field of view of FIS 40. If not, the patient is repositioned relative to FIS 40, e.g. fluoroscope detector 42, in a repositioning step 160, using the instructions provided by processor 36. The position of the heart after repositioning the patient is remapped in mapping step 130. If the image of the heart appears in the display, no further action is needed. The fluoroscope position calibration is terminated in a terminating step 170.

Although the embodiments described herein mainly address synchronized fluoroscopic imaging and catheter tracking systems, the methods and systems described herein can also be used in any suitable type of imaging system for monitoring medical devices, which are navigated in a living body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for calibrating a position of a fluoroscopic imaging system having a field of view so that a region of interest of a patient body is at a center of the field of view, said method comprising:
   (i) registering the fluoroscopic imaging system to a common frame of reference using a fluoroscopic image and position data by imaging using the fluoroscopic imaging system one or more objects having known coordinates in a first coordinate system of a position tracking system, and registering the first coordinate system of the position tracking system with a second coordinate system of the fluoroscopic imaging system:
   (ii) marking a region of interest in a patient body comprising measuring using respective positions of one or more sensors of the position tracking system that are positioned at known locations relative to the region of interest;
   (iii) setting the field of view of the fluoroscopic imaging system such that the region of interest appears at a center of the field of view wherein setting the field of view includes subsequent repositioning of the patient body without applying any fluoroscopic radiation to the patient relative to the fluoroscopic imaging system in accord with instructions provided by a processor when the region of interest did not previously appear centered in the field of view of the fluoroscopic imaging system;
   (iv) calculating a median location of a plurality of intra-body probes within the body of the patient, and estimating a location of the region of interest based on the median location.

2. The method according to claim 1, wherein setting the field of view comprises positioning the fluoroscopic imaging system relative to the patient, without irradiating the patient body with the fluoroscopic imaging system.

3. The method according to claim 1, wherein measuring the positions comprises locating one or more skin patch sensors of the position tracking system that are applied on a surface of the patient body.

4. The method according to claim 1, wherein measuring the region of interest comprises marking a fixed location in a three dimensional map of the region of interest in the patient body produced by the position tracking system.

5. The method according to claim 1, wherein setting the field of view comprises repositioning the patient body relative to the fluoroscopic imaging system so as to provide a largest overlap between the region of interest and the field of view.

6. The method according to claim 1, wherein the one or more objects are one or more magnetic field generators positioned near the patient body.

7. A fluoroscopic position calibration system for calibrating a position of a fluoroscopic imaging system having a field of view so that a region of interest of a patient body is at a center of the field of view, said apparatus comprising:
   an interface for communicating with a fluoroscopic imaging system and a position tracking system; and
   a processor which is configured to register the fluoroscopic imaging system and a position tracking system to common frame of reference using a fluoroscopic image and position data to a common frame of reference by imaging using the fluoroscopic imaging system one or more objects having known coordinates in a first coordinate system of the position tracking system, and registering the first coordinate system of the position tracking system with a second coordinate system of the fluoroscopic imaging system; to mark a region of interest in a patient body comprising measuring using respective positions of one or more sensors of the position tracking system that are positioned at known locations relative to the region of interest, and to set the field of view of the fluoroscopic imaging system such that the region of interest appears at a center of the field of view wherein to set the field of view includes subsequent repositioning of the patient body without applying any fluoroscopic radiation to the patient relative to the fluoroscopic imaging system in accord with instructions provided by the processor when the region of interest did not previously appear centered in the field of view of fluoroscopic imaging system;
   wherein the processor is further configured to calculate the median location of a plurality of intra-body probes within the body of the patient, and to estimate a location of the region of interest based on the median location.

8. The apparatus according to claim 7, wherein the processor is configured to set the field of view without irradiating the patient with the fluoroscopic imaging system.

9. The apparatus according to claim 7, wherein the processor is configured to measure the positions by locating one or more skin patch sensors of the position tracking system that are applied on a surface of the patient body.

10. The apparatus according to claim 7, wherein the processor is configured to identify the region of interest as a fixed location in a three dimensional map of the region of interest in the patient's body produced by the position tracking system.

11. The apparatus according to claim 7, wherein the processor is configured to set the field of view by repositioning the patient body relative to the fluoroscopic imaging system so as to provide a largest overlap between the region of interest and the field of view.

12. The apparatus according to claim 7, wherein the one or more objects are one or more magnetic field generators positioned near the patient body.

13. A system comprising:
    a position tracking system;
    a fluoroscopic tracking system; and
    a fluoroscopic position calibration system for calibrating a position of a fluoroscopic imaging system having a field of view so that a region of interest of a patient body is at a center of the field of view, said apparatus comprising:
    an interface for communicating with a fluoroscopic imaging system and a position tracking system; and
    a processor which is configured to register the fluoroscopic imaging system and a position tracking system to common frame of reference using a fluoroscopic image and position data to a common frame of reference by imaging using the fluoroscopic imaging system one or more objects having known coordinates in a first coordinate system of the position tracking system, and registering the first coordinate system of the position tracking system with a second coordinate system of the fluoroscopic imaging system to mark a region of interest in a patient body comprising measuring using respective positions of one or more sensors of the position tracking system that are positioned at known locations relative to the region of interest, and to set the field of view of the fluoroscopic imaging system such that the region of interest appears at a center of the field of view wherein to set the field of view includes subsequent repositioning of the patient body without applying any fluoroscopic radiation to the patient relative to the fluoroscopic imaging system in accord with instructions provided by the processor when the region of interest did not previously appear centered in the field of view of fluoroscopic imaging system;

wherein the processor is further configured to calculate the median location of a plurality of intra-body probes within the body of the patient, and to estimate a location of the region of interest based on the median location.

14. The system according to claim 13, wherein the one or more objects are one or more magnetic field generators positioned near the patient body.

\* \* \* \* \*